United States Patent
Chen et al.

(10) Patent No.: US 11,998,279 B2
(45) Date of Patent: Jun. 4, 2024

(54) METHOD AND SYSTEM OF TRACKING PATIENT POSITION IN OPERATION

(71) Applicant: BRAIN NAVI BIOTECHNOLOGY CO., LTD, Hsinchu County (TW)

(72) Inventors: Chieh Hsiao Chen, Santa Clara, CA (US); Kuan Ju Wang, Santa Clara, CA (US)

(73) Assignee: Brain Navi Biotechnology Co., Ltd., Zhubei (TW)

(*) Notice: Subject to any disclaimer, the term of this patent is extended or adjusted under 35 U.S.C. 154(b) by 749 days.

(21) Appl. No.: 17/263,855

(22) PCT Filed: Jul. 31, 2019

(86) PCT No.: PCT/CN2019/098706
§ 371 (c)(1),
(2) Date: Jan. 27, 2021

(87) PCT Pub. No.: WO2020/025001
PCT Pub. Date: Feb. 6, 2020

(65) Prior Publication Data
US 2021/0307832 A1  Oct. 7, 2021

(51) Int. Cl.
*A61B 34/10* (2016.01)
*A61B 34/30* (2016.01)
*A61B 90/00* (2016.01)

(52) U.S. Cl.
CPC ............. *A61B 34/10* (2016.02); *A61B 34/30* (2016.02); *A61B 90/36* (2016.02); *A61B 90/39* (2016.02);
(Continued)

(58) Field of Classification Search
CPC ......... A61B 34/10; A61B 34/30; A61B 90/36; A61B 90/39; A61B 2034/107; A61B 2090/364; A61B 2090/3983
See application file for complete search history.

(56) References Cited

U.S. PATENT DOCUMENTS

2014/0112529 A1* 4/2014 Park ..................... G06T 7/33
 382/106
2016/0067525 A1* 3/2016 Bouchet ............... A61N 5/1069
 600/1
(Continued)

FOREIGN PATENT DOCUMENTS

CN   103997982 A   8/2014
CN   104083217 A   10/2014
(Continued)

OTHER PUBLICATIONS

The Notification of Transmittal of the International Search Report and the Written Opinion of the Internation Searching Authority, or the Declaration dated Oct. 29, 2019 from PCT Patent Application No. PCT/CN2019/098706.

*Primary Examiner* — Kira Nguyen
(74) *Attorney, Agent, or Firm* — Haverstock & Owens, A Law Corporation

(57) ABSTRACT

Embodiments of the present invention set forth a method to update an operation pathway for a robotic arm assembly in response to a movement of a patient. The method includes processing a two-dimensional image associated with a tag having a spatial relationship with the patient. A corresponding movement of the tag in response to the movement of the patient is determined based on the spatial relationship. The tag includes a first point and a second point and the two-dimensional image includes a first point image and a second point image. The method also includes associating the first point image with the first point and the second point image with the second point and updating the operation pathway based on a conversion matrix of the first point and the second point, and the first point image and the second point image.

15 Claims, 7 Drawing Sheets

(52) U.S. Cl.
CPC ... *A61B 2034/107* (2016.02); *A61B 2090/364* (2016.02); *A61B 2090/3983* (2016.02)

(56) References Cited

U.S. PATENT DOCUMENTS

| | | | |
|---|---|---|---|
| 2016/0278865 A1* | 9/2016 | Capote | A61B 46/00 |
| 2016/0354157 A1* | 12/2016 | Chen | G06T 7/73 |
| 2017/0265943 A1* | 9/2017 | Sela | A61B 34/20 |
| 2018/0000546 A1* | 1/2018 | Crawford | A61B 10/0233 |
| 2018/0092699 A1 | 4/2018 | Finley | |
| 2019/0000569 A1* | 1/2019 | Crawford | A61B 34/20 |
| 2019/0142359 A1* | 5/2019 | Zhang | A61B 34/20 606/130 |
| 2021/0345893 A1* | 11/2021 | Bishop | G16H 20/40 |

FOREIGN PATENT DOCUMENTS

| | | |
|---|---|---|
| CN | 106236258 A | 12/2016 |
| CN | 106890025 A | 6/2017 |

* cited by examiner

METHOD AND SYSTEM OF TRACKING PATIENT POSITION IN OPERATION

CROSS-REFERENCE TO RELATED APPLICATIONS

This application claims the benefit of U.S. Provisional Application No. 62/713,522, filed Aug. 1, 2018 and U.S. Provisional Application No. 62/820,804, filed Mar. 19, 2019, which are incorporated by reference in their entirety.

BACKGROUND OF THE INVENTION

Field of the Invention

Embodiments of the present invention relate generally to methods and systems of tracking a position or an orientation of a patient in an operation.

Description of the Related Art

Unless otherwise indicated herein, the approaches described in this section are not prior art to the claims in this application and are not admitted to be prior art by inclusion in this section.

To perform an operation, a plan of an operation pathway is critical. Robotic operation may offer a precise control of the operation pathway. Before the operation, patient is subjected to a medical scan (e.g., CT or MRI). The operation pathway to the desired anatomical region is planned based on the medical scan. Artificial intelligence may be employed to suggest the surgeon with optimal routes that incur the least amount of damages. To perform the operation, the position of the patient may be matched to the perspective of the medical scan to accurate perform the operation along the planned operation pathway.

However, in the operation, the position of the patient may be moved. Accordingly, the planned operation pathway may not be applicable in view of the moved position of the patient and may be updated in response to the moved position of the patient.

DETAILED DESCRIPTION

Figure 1:
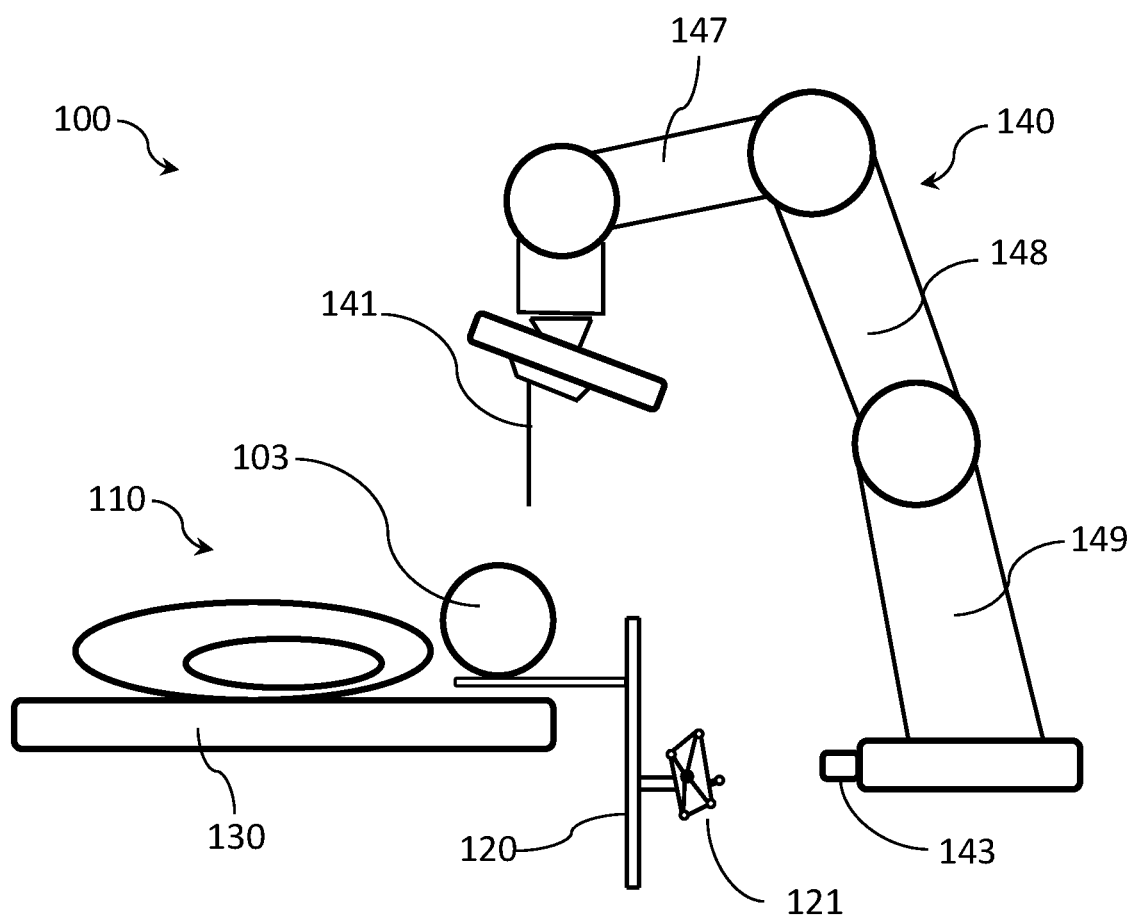
FIG. 1 is an example figure showing an operation system configured to perform an operation on a patient.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

FIG. 1 is an example figure showing operation system 100 configured to perform an operation on patient 101, arranged in accordance with some embodiments of the present disclosure. In some embodiments, operation system 100 includes frame 120, operating table 130 and robotic arm assembly 140.

In some embodiments, frame 120 is configured to support and attach to an operation target (e.g., patient's head 103) of patient 110. In addition, frame 120 is also configured to attach to operating table 130. In some embodiments, frame 120 further includes tag 121. Tag 121 is fixed or integrally formed with frame 120. Therefore, patient's head 103, operating table 130, frame 120 and tag 121 together may form a predetermined spatial relationship. In other words, in response to a first movement of patient's head 103, tag 121 also has a corresponding second movement based on the predetermined spatial relationship. Accordingly, the movement of tag 121 may also be used to determine whether the patient's head has moved.

In some embodiments, frame 121 may include more than one tags. Each tag may include a unique identification pattern from each other. Accordingly, operating system 100 may process different requirements based on these tags.

In some embodiments, robotic arm assembly 140 may include surgical instrument 141, optical apparatus 143, first arm 147, second arm 148 and third arm 149. In some embodiments, optical apparatus 143 is an IR camera capable of capturing images of tag 121 at different times. These captured images are processed to identify whether a movement of tag 121 exceeds a threshold. In response to determining the movement of tag 121 exceeding the threshold, a processor (not shown) associated with robotic arm assembly 140 may determine that patient 110 has moved based on the predetermined spatial relationship set forth above and issue a command to robotic arm assembly 140 to stop the operation and move to a safety point which will not cause harms to patient 110. In response to the determination that patient 110 has moved, the processor may calculate a new operation pathway and issue a command to robotic arm assembly 140 to move from the safety point along the new operation pathway.

Figure 2:
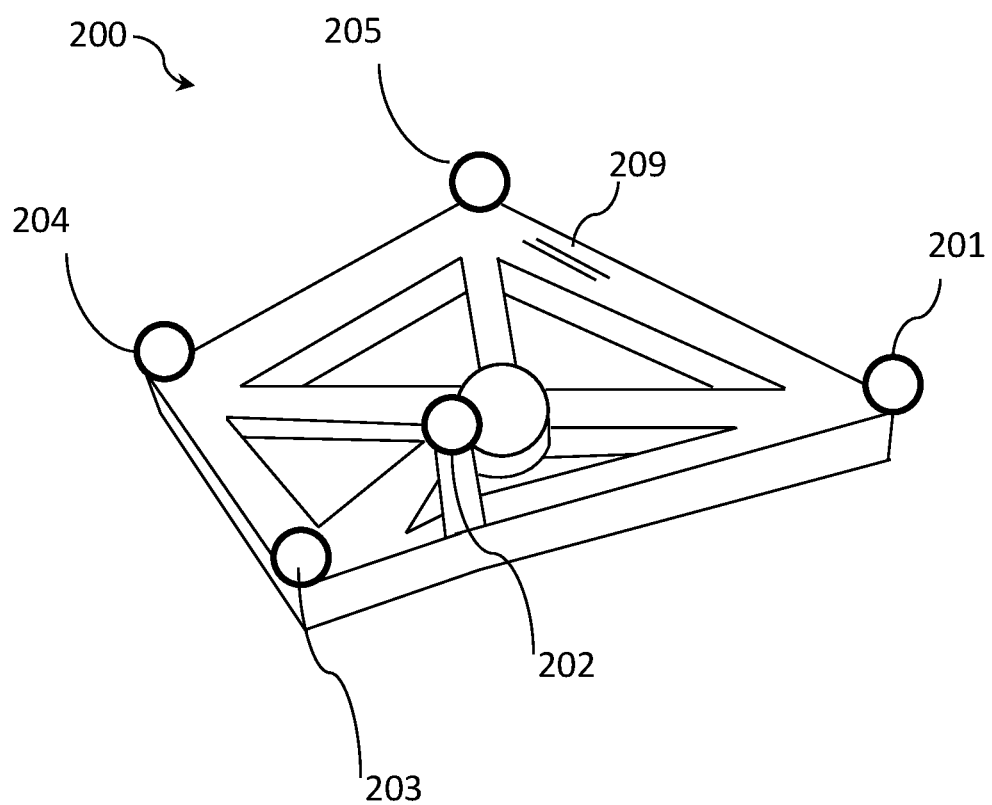
FIG. 2 is an example figure showing a tag.

FIG. 2 is an example figure showing tag 200, arranged in accordance with some embodiments of the present disclosure. Tag 200 may correspond to tag 121 of FIG. 1. In some embodiments, tag 200 includes point 201, point 202, point 203, point 204, point 205 and identification pattern 209. Points 201, 202, 203, 204, 205 and identification pattern 209 may emit lights having specific wavelengths which can be captured by an optical apparatus (e.g., optical apparatus 143). On the contrary, other parts of tag 200 emit very few such lights and therefore may be barely captured by the optical apparatus. In some other embodiments, points 201, 202, 203, 204, 205 and identification pattern 209 may reflect lights generated by a light source having specific wavelengths which can be captured by an optical apparatus (e.g., optical apparatus 143). Other parts of tag 200 may absorb such lights and therefore may be barely captured by the optical apparatus.

Figure 3A:
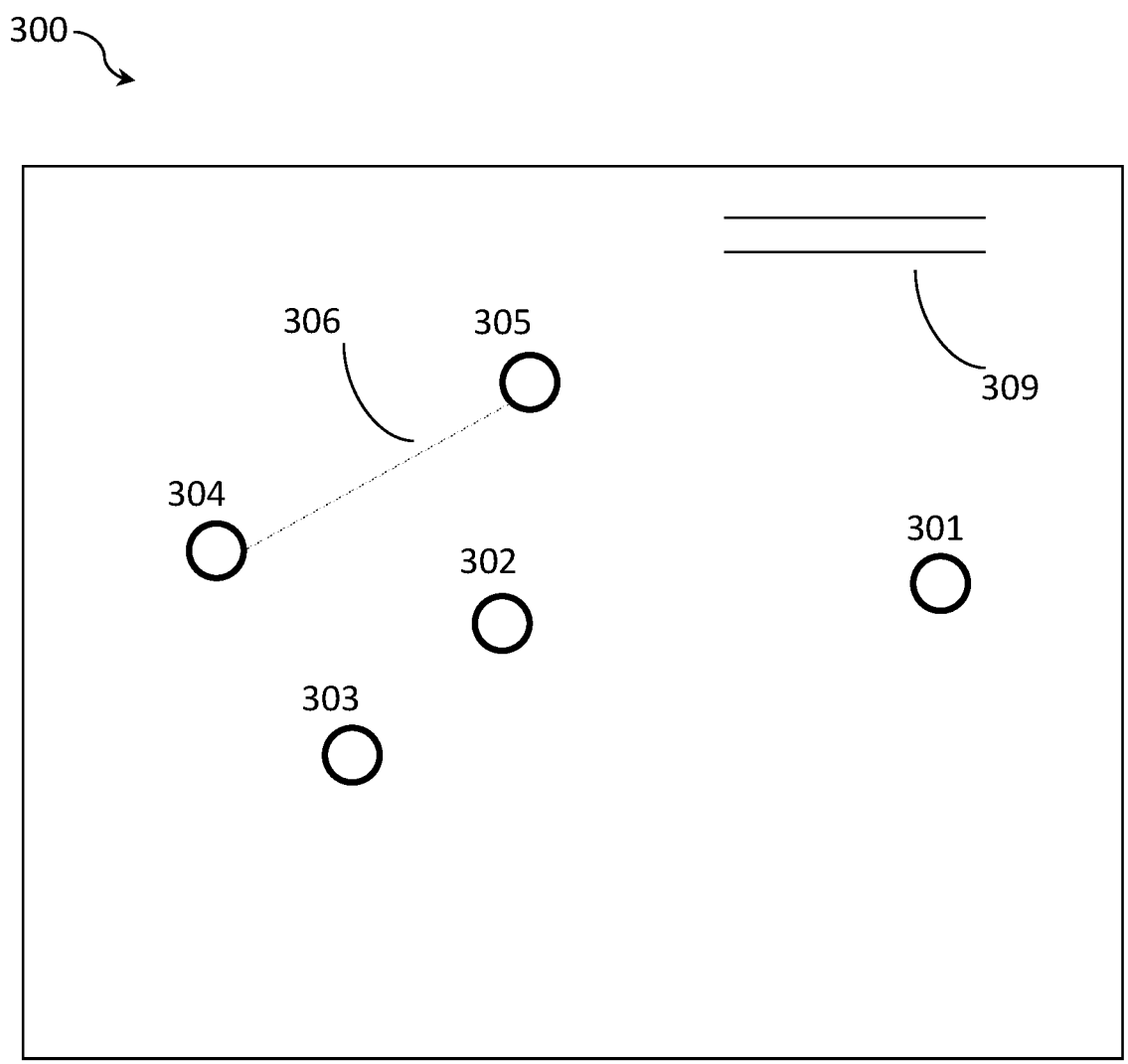
FIG. 3A is an example image of a tag captured by an optical apparatus.

FIG. 3A is an example image 300 of a tag captured by an optical apparatus, arranged in accordance with some embodiments of the present disclosure. Image 300 may include point images 301, 302, 303, 304 and 305, bar image 306 between points images 304 and 305 and identification image 309. It has been a challenge to associate point images 301, 302, 303, 304 and 305 to points 201, 202, 203, 204 and 205 efficiently and correctly.

In some embodiments, point image 301 may correspond to an image of point 201. Similarly, point image 302 may correspond to an image of point 202, point image 303 may correspond to an image of point 203, point image 304 may correspond to an image of point 204, and point image 305 may correspond to an image of point 205. Bar image 306 may correspond to parts of tag 200 between points 204 and 205.

Figure 3B:
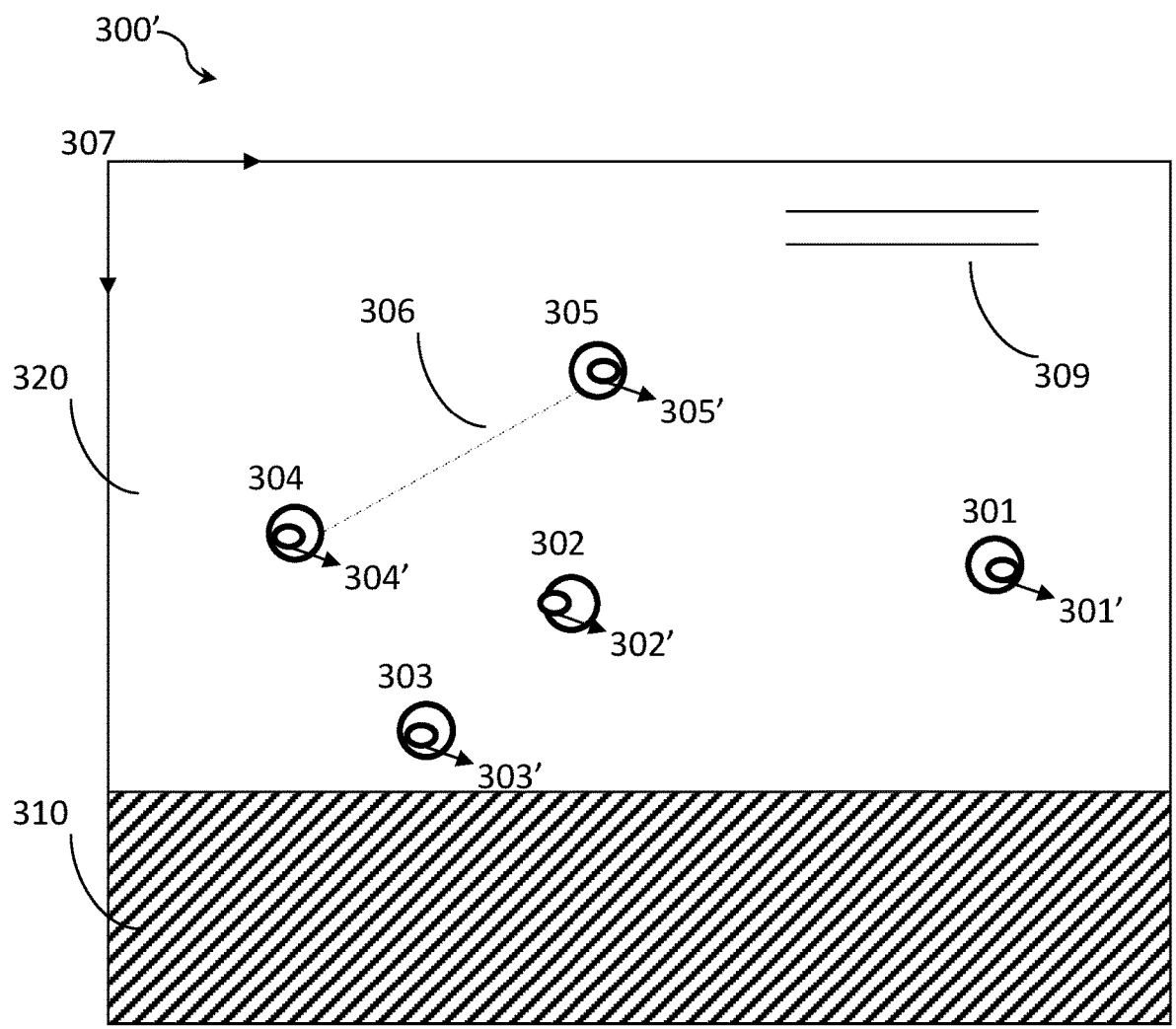
FIG. 3B is an example processed image of a tag captured by an optical apparatus.
Figure 4:
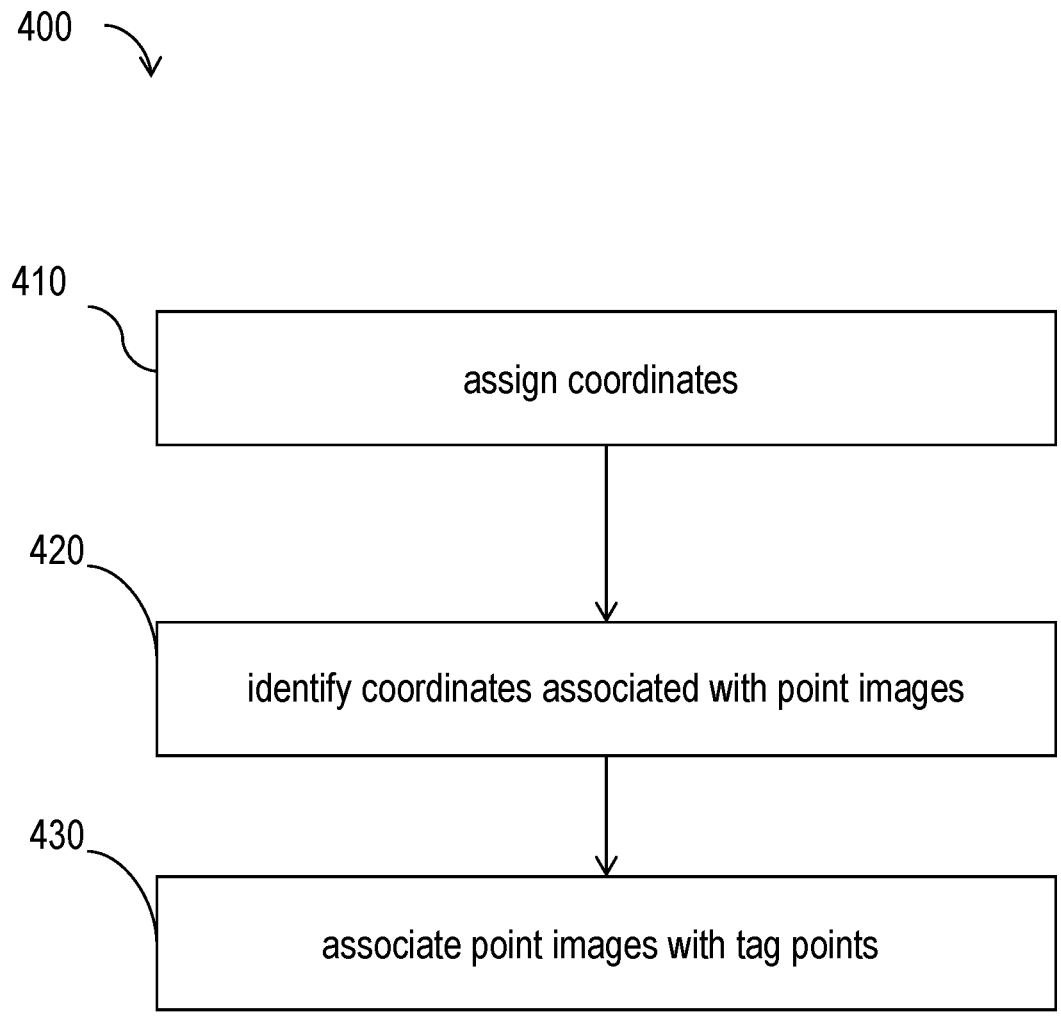
FIG. 4 is a flow diagram illustrating an example process to process a two-dimensional image associated with a tag.

Identification image 309 may correspond to identification pattern 209. FIG. 3B is an example processed image 300' of a tag captured by an optical apparatus and FIG. 4 is a flow diagram illustrating an example process 400 to process a two-dimensional image associated with a tag, all arranged in accordance with some embodiments of the present disclosure. Process 400 may include one or more operations, functions, or actions as illustrated by blocks 410, 420 and/or 430, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein. In conjunction with FIG. 3B, FIG. 4 will be further described in details below.

Process 400 may begin at block 410, "assign coordinates." Referring to FIG. 3A, in some embodiments, image 300 is a two-dimensional image associated with tag 200. In FIG. 3B, image 300' may be a processed image 300. In some embodiments, a two-dimensional coordinate system is assigned to image 300'. In some embodiments, the upper left corner 307 is assigned as the origin point (0, 0) of the two-dimensional coordinate system. The two-dimensional coordinate system may be based on pixels of image 300. Therefore, point images 301, 302, 303, 304 and 305 on image 300 may be described by the two-dimensional coordinate system.

Block 410 may be followed by block 420 "identify coordinates associated with point images." In some embodiments, to efficiently identify point images 301, 302, 303, 304 and 305 from image 300', thresholding techniques may be applied. For example, image 300' is first processed with blocks including many pixels. In some embodiments, blocks not including any pixel having an intensity greater than a threshold (e.g., region 310 or bar image 306) are discarded from further processing to save the computation resources. Blocks including pixels having an intensity greater than the threshold (e.g., region 320) are then further processed on a pixel basis.

In some embodiments, region 320 may be enlarged with an enlargement factor. Therefore, point images 301, 302, 303, 304 and 305 may be also enlarged with the enlargement factor. In some embodiments, additional thresholding techniques may be applied to pixels of the enlarged point images to identify one or more pixels that have a greater intensity. Image associated with the identified pixels may be shrunk back to the two-dimensional system based on a shrinkage factor (e.g., reciprocal of the enlargement factor). Therefore, new point images 301', 302', 303', 304' and 305' with higher intensity may be identified on image 300 and coordinates of the two-dimensional coordinate system may be assigned to point images 301', 302', 303', 304' and 305'. In some embodiments, point image 301' is assigned coordinates $(X_{301'}, Y_{301'})$ on the two-dimensional coordinate system. Similarly, point image 302' is assigned coordinates $(X_{302'}, Y_{302'})$, point image 303' is assigned coordinates $(X_{303'}, Y_{303'})$, point image 304' is assigned coordinates $(X_{304'}, Y_{304})$, and point image 305' is assigned coordinates $(X_{305'}, Y 305)$, respectively.

Block 420 may be followed by block 430 "associate point images with tag points." In some embodiments, point images 301', 302', 303', 304' and 305' are associated with points 201, 202, 203, 204 and 205. In some embodiments, based on perspective-n-point approaches, coordinates of point images 301', 302', 303', 304' and 305' on the two-dimensional coordinate system and coordinates of points 201, 202, 203, 204 and 205 of tag 121 on a three-dimensional coordinate system which describes the spatial relationship among optical apparatus 143, robotic arm assembly 140 and surgical instrument 141, a conversion matrix describing a relationship between a point image in image 300' and its associated point at tag 200 may be established.

Figure 5:
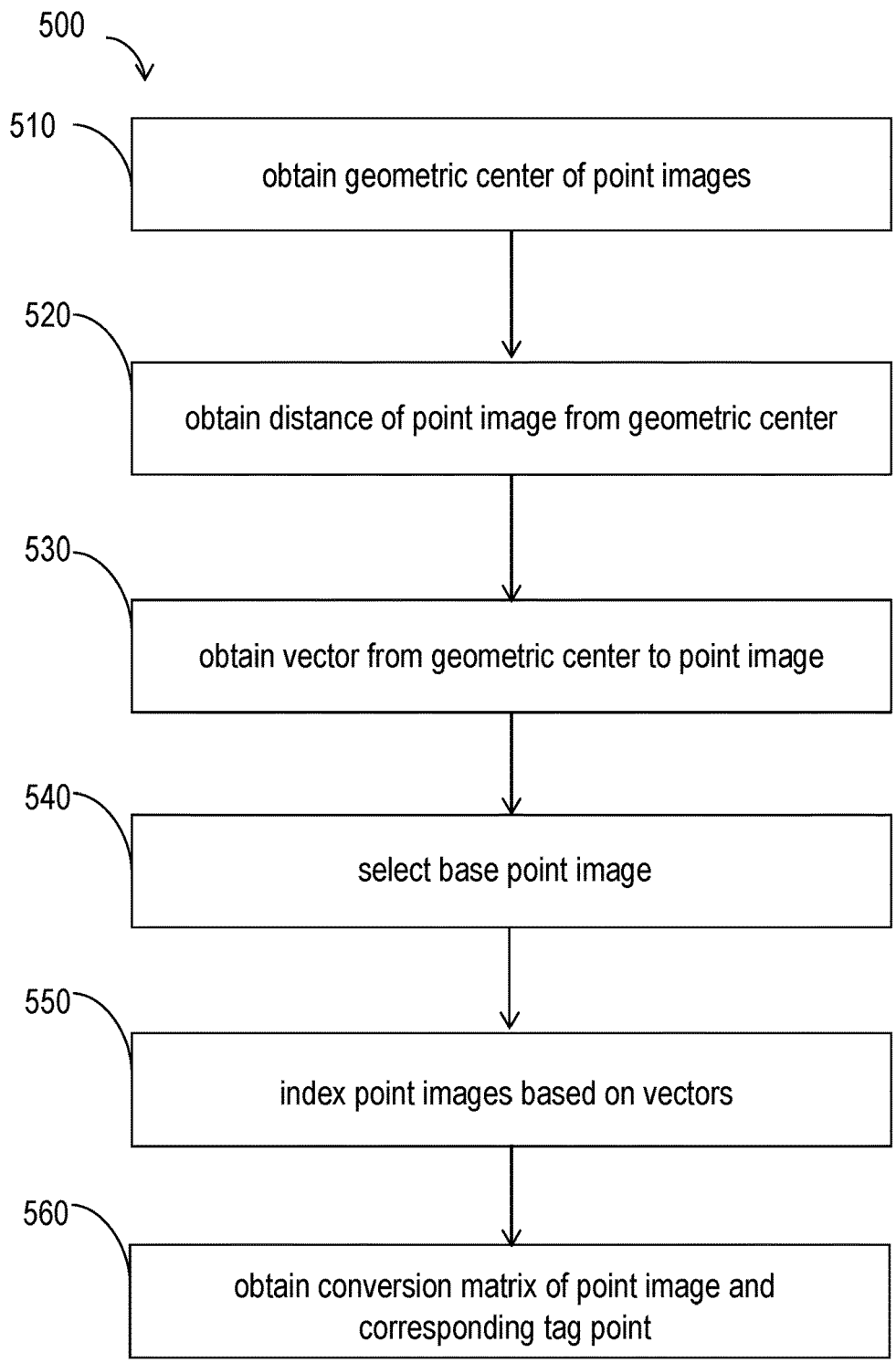
FIG. 5 is a flow diagram illustrating an example process to associate point images with points of a tag.

FIG. 5 is a flow diagram illustrating an example process 500 to associate point images with points of a tag, arranged in accordance with some embodiments of the present disclosure. Process 500 may include one or more operations, functions, or actions as illustrated by blocks 510, 520, 530, 540, 550 and/or 560, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 500 may begin at block 510, "obtain geometric center of point images." In some embodiments, as set forth above, in the two-dimensional coordinate system, point images 301', 302', 303', 304' and 305' have coordinates $(X_{301'}, Y_{301'})$, $(X_{302'}, Y_{302'})$, $(X_{303'}, Y_{303'})$, $(X_{304'}, Y_{304})$ and $(X_{305'}, Y_{305'})$, respectively. A geometric center of point images 301', 302', 303', 304' and 305' may have coordinates $((X_{301'}+X_{302'}+X_{303'}+X_{304'}+X_{305'})/5, (Y_{301'}+Y_{302'}+Y_{303'}+Y_{304'}+Y_{305'})/5)$.

Block 510 may be followed by block 520, "obtain distance of point image from geometric center." In some embodiments, a first distance between point image 301' and the geometric center is obtained as $$[X_{301'}-X_{301'}+X_{302'}+X_{303'}+X_{304'}+X_{305'}/5]^2+[Y_{301'}-Y_{301'}+Y_{302'}+Y_{303'}+Y_{304'}+Y_{305'}/5]^2.$$

Similarly, a second distance between point image 302' and the geometric center, a third distance between point image 303' and the geometric center, a fourth distance between point image 304' and the geometric center and a fifth distance between point image 305' and the geometric center may be obtained.

Block 520 may be followed by block 530, "obtain vector from geometric center to point image." In some embodiments, a first vector $\overline{Geometriccenter301'}$ from the geometric center to point image 301' is obtained as $(X_{301'}-(X_{301'}+X_{302'}+X_{303'}+X_{304'}+X_{305'})/5, Y_{301'}-(Y_{301'}+Y_{302'}+Y_{303'}+Y_{304'}+Y_{305'})/5)$. Similarly, a second vector $\overline{Geometriccenter302'}$ from the geometric center to point image 302', a third vector $\overline{Geometriccenter303'}$ from the geometric center to point image 303', a fourth vector $\overline{Geometriccenter304'}$ from the geometric center to point image 304' and a fifth vector $\overline{Geometriccenter304'}$ from the geometric center to point image 305' may be also obtained.

Block 530 may be followed by block 540, "select base point image." In some embodiments, the first distance, the second distance, the third distance, the fourth distance and the fifth distance obtained in block 520 are compared to select which point image is the base point image. In some embodiments, the point image having the farthest distance from the geometric center in the two-dimensional coordinate system may be selected as the base point. Alternatively, the point image having the closest distance from the geometric center in the two-dimensional coordinate system may be selected as the base point. In some other embodiments, the base point may be selected based on a relationship between identification image 309 and point images 301', 302', 303', 304' and 305' in the two-dimensional coordinate system. For illustration only, in some embodiments, point image 301' is selected as the base point image.

Block 540 may be followed by block 550, "index point images based on vectors." In some embodiments, a cross product of the first vector (e.g., $\overline{Geometriccenter301'}$) and the second vector (e.g., $\overline{Geometriccenter302'}$) may be used to determine whether point image 302' is along the clockwise direction from point image 301'. In some embodiments, in response to a cross product of the first vector and the second vector being a vector pointing to the positive z direction with respect to the two-dimensional coordinate system, point image 302' is determined along the clockwise direction from point image 301'. In some other embodiments, a dot product of the first vector (e.g., $\overline{Geometriccenter301'}$) and the second vector (e.g., $\overline{Geometriccenter302'}$) may be used to determine an angle between the first vector and the second vector. Therefore, based on the cross product and the dot product, point image 302' may be determined at a first angle along the clockwise direction from point image 301'. Similarly, point images 303', 304' and 305' may be determined at a second angle, a third angle and a fourth angle along the clockwise direction from point image 301', respectively. In some embodiments, based on a comparison between the first angle, the second angle, the third angle and the fourth angle, a sequence of point images 301', 302', 303', 304' and 305' along the clockwise direction may be determined. For example, in response to the first angle is smaller than the second angle, point image 302' is determined to be closer to point image 301' along the clockwise direction than point 303'. After the sequence is determined, point images 301', 302', 303', 304' and 305' may be indexed according to the sequence.

Block 550 may be followed by block 560, "obtain conversion matrix of point image and corresponding tag point." In some embodiments, based on the index obtained in block 550 and perspective-n-point approaches, a conversion matrix which describes a mathematical relationship between coordinates of points of tag 200 (e.g., 201, 202, 203, 204 and 205) in a three-dimensional coordinate system and their corresponding point image (e.g., 301', 302', 303', 304' and 305') may be established. Referring back to FIG. 1, in some embodiments, the three-dimensional coordinate system may describe the spatial relationship among optical apparatus 143, robotic arm assembly 140 and surgical instrument 141.

Figure 6:
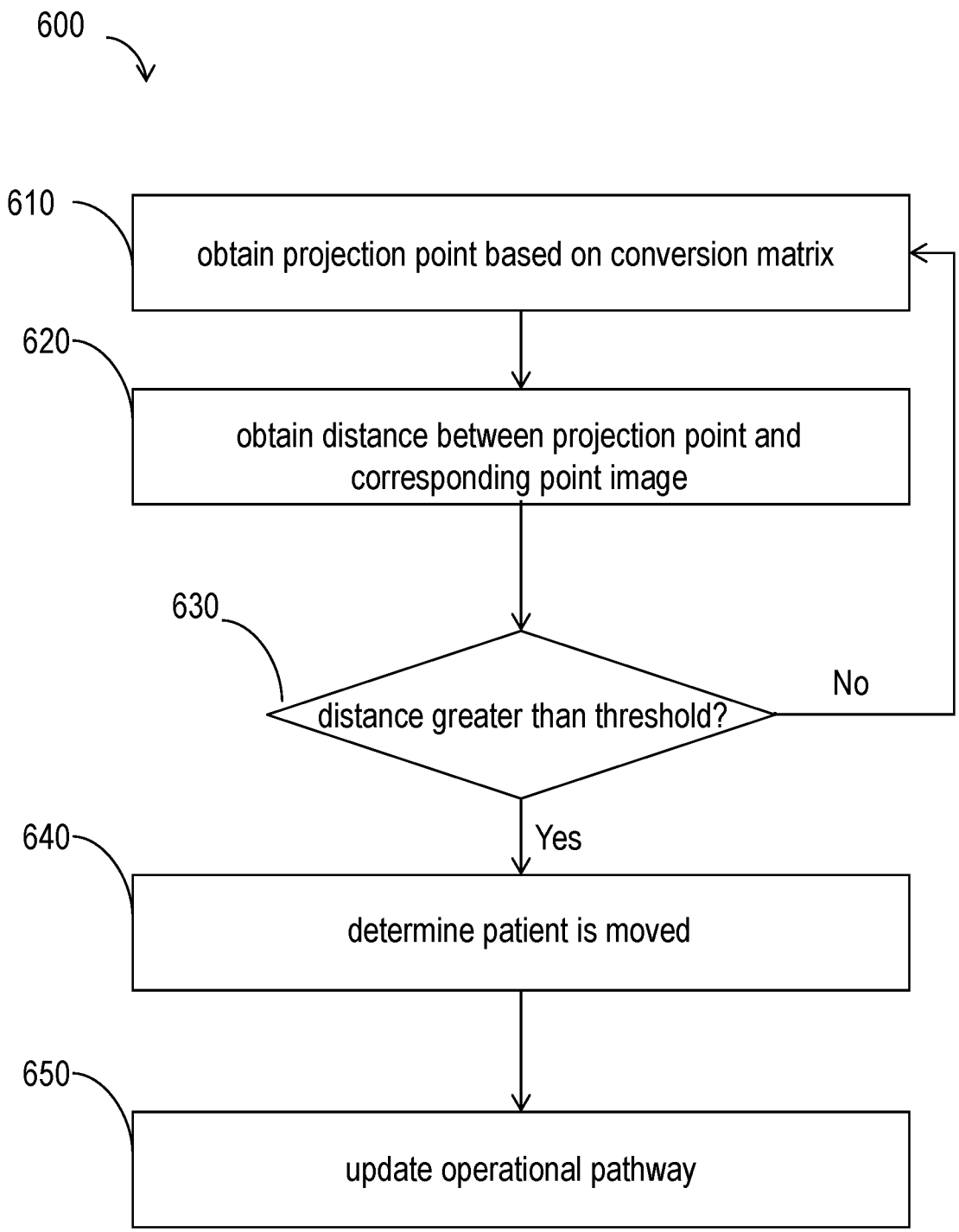
FIG. 6 is a flow diagram illustrating an example process to update an operation pathway in response to a movement of a patient based on a plurality of conversion matrices, all arranged in accordance with some embodiments of the present disclosure.

FIG. 6 is a flow diagram illustrating an example process 600 to update an operation pathway in response to a movement of a patient based on a plurality of conversion matrices, arranged in accordance with some embodiments of the present disclosure. Process 600 may include one or more operations, functions, or actions as illustrated by blocks 610, 620, 630, 640 and/or 650, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 600 may begin at block 610, "obtain projection point based on conversion matrix." In some embodiments, after obtaining the conversion matrix, a first projection point of point 201 according to the conversion matrix may be obtained. In some embodiments, the projection point has coordinates $(X_{301'''}, Y_{301'''})$ in the two-dimensional coordinate system. Similarly, a second projection point of point 202, a third projection point of point 203, a fourth projection point of point 204 and a fifth projection point of point 205 may also be obtained and has coordinates $(X_{302'''}, Y_{302'''})$, $(X_{303'''}, Y_{303'''})$, $(X_{304'''}, Y_{304'''})$ and $(X_{305'''}, Y_{305'''})$ in the two-dimensional coordinate system, respectively.

Block 610 may be followed by block 620, "obtain distance between projection point and corresponding point image." In some embodiments, a first distance between the first projection point having coordinates $(X_{301'''}, Y_{301'''})$ and point image 301' having coordinates $(X_{301'}, Y_{301'})$ is calculated. Similarly, a second distance between the second projection point having coordinates $(X_{302'''}, Y_{302'''})$ and point image 302' having coordinates $(X_{302'}, Y_{302'})$, a third distance between the second projection point having coordinates $(X_{303'''}, Y_{303'''})$ and point image 303' having coordinates $(X_{303'}, Y_{303'})$, a fourth distance between the fourth projection point having coordinates $(X_{304'''}, Y_{304'''})$ and point image 304' having coordinates $(X_{304'}, Y_{304})$ and a fifth distance between the fifth projection point having coordinates $(X_{305'''}, Y_{305'''})$ and point image 305' having coordinates $(X_{305'}, Y_{305})$ may be also obtained, respectively.

Block 620 may be followed by block 630, "distance greater than threshold?" In some embodiments, in response to a sum of the first distance, the second distance, the third distance, the fourth distance and the fifth distance is greater than a threshold, block 630 may be followed by block 640, "determine patient is moved."

In some other embodiments, in response to a sum of the first distance, the second distance, the third distance, the fourth distance and the fifth distance not greater than a threshold, block 630 may be followed by block 610, "obtain projection point based on conversion matrix." After obtaining another conversion matrix associated with image 300/300' captured at a second time, another set of projection points having coordinates in the two-dimensional coordinate system of points 201, 202, 203, 204 and 205 may be obtained according to another conversion matrix.

Block 640 may be followed by block 650, "update operation pathway." In some embodiments, referring back to FIG. 1, robotic arm assembly 140 may move to a safety point which will not cause harms to patient 110. A new operation pathway may be updated in response to the movement of patient 110 and robotic arm assembly 140 is then configured to move from the safety point along the updated operation pathway.

In some other embodiments, the updated operation pathway may be verified so that the updated operation pathway will not cause a collision between surgical instrument 141 and robotic arm assembly 140. Alternatively, referring back to FIG. 1, the updated operation pathway may be verified so that the updated operation pathway will not cause a collision among first arm 147, second arm 148 and third arm 149 of robotic arm assembly 140.

In response to the updated operation pathway is verified to cause a collision of robotic arm assembly 140, the updated operation pathway will be abandoned and a new updated operation pathway will be calculated.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

We claim:

1. A method to update an operation pathway for a robotic arm assembly to perform an operation on a patient having a predetermined spatial relationship with a frame including a tag in response to a movement of the patient, comprising:
   processing a two-dimensional image associated with the tag having the spatial relationship with the patient, wherein a corresponding movement of the tag in response to the movement of the patient is determined based on the spatial relationship, and wherein the tag includes a first point and a second point, and the two-dimensional image includes a first point image and a second point image;
   associating the first point image with the first point and the second point image with the second point; and
   updating the operation pathway based on a conversion matrix of the first point and the second point, and the first point image and the second point image;
   wherein the updating the operation pathway further includes:
      obtaining a first projection point associated with the first point and a second projection point associated with the second point in the two-dimensional coordinate system based on the conversion matrix;
      obtaining a third distance between the first projection point and the first point image in the two-dimensional coordinate system; and
      obtaining a fourth distance between the second projection point and the second point image in the two-dimensional coordinate system;
   wherein the method further comprises in response to a sum of the third distance and the fourth distance greater than a second threshold, identifying the movement of the patient and updating the operation pathway.

2. The method of claim 1, wherein the processing the two-dimensional image further includes identifying the first point image and the second point image having intensities greater than a first threshold based on an enlargement factor and a shrinkage factor.

3. The method of claim 1, wherein the processing two-dimensional image further includes assigning a two-dimensional coordinate system to the two-dimensional image and identifying coordinates associated with the first point image and the second point image in the two-dimensional coordinate system.

4. The method of claim 1, wherein the associating the first point image with the first point further comprises:
   obtaining a geometric center associated with the first point image and the second point image in the two-dimensional coordinate system;
   obtaining a first distance between the first point image and the geometric center and a second distance between the second point image and the geometric center; and
   selecting the first point image as a base point image based on the first distance and the second distance.

5. The method of claim 1, wherein the associating the second point image with the second point further comprises:
   obtaining a first vector from the geometric center to the first point image in the two-dimensional coordinate system;
   obtaining a second vector from the geometric center to the second point image in the two-dimensional coordinate system; and
   associating the second point image with the second point based on a cross product of the first vector and the second vector and a dot project of the first vector and the second vector.

6. The method of claim 1, the method further comprising:
   in response to identifying the movement of the patient, moving the robotic arm assembly to a safety point; and moving the robotic arm assembly from the safety point to an operation target of the patient based on the updated operation pathway.

7. The method of claim 1, the method further comprising verifying the updated operation pathway to identify a collision associated with the robotic arm assembly.

8. The system of claim 1, wherein the processor is further configured to verify the updated operation pathway to identify a collision associated with the robotic arm assembly.

9. A system to update an operation pathway for a robotic arm assembly to perform an operation on a patient having a predetermined spatial relationship with a frame including a tag in response to a movement of the patient, comprising:
an optical apparatus; and
a processor configured to:
process a two-dimensional image associated with the tag having the spatial relationship with the patient, wherein a corresponding movement of the tag in response to the movement of the patient is determined based on the spatial relationship, and wherein the tag includes a first point and a second point, and the two-dimensional image includes a first point image and a second point image;
associate the first point image with the first point and the second point image with the second point; and
update the operation pathway based on a conversion matrix of the first point and the second point, and the first point image and the second point image;
wherein the processor is further configured to:
obtain a first projection point associated with the first point and a second projection point associated with the second point in the two-dimensional coordinate system based on the conversion matrix;
obtain a third distance between the first projection point and the first point image in the two-dimensional coordinate system;
obtain a fourth distance between the second projection point and the second point image in the two-dimensional coordinate system; and
identify the movement of the patient and update the operation pathway in response to a sum of the third distance and the fourth distance greater than a second threshold.

10. The system of claim 9, wherein the processor is further configured to identify the first point image and the second point image having intensities greater than a first threshold based on an enlargement factor and a shrinkage factor.

11. The system of claim 9, wherein the processor is further configured to assign a two-dimensional coordinate system to the two-dimensional image and identify coordinates associated with the first point image and the second point image in the two-dimensional coordinate system.

12. The system of claim 9, wherein the processor is further configured to:
obtain a geometric center associated with the first point image and the second point image in the two-dimensional coordinate system;
obtain a first distance between the first point image and the geometric center and a second distance between the second point image and the geometric center; and
select the first point image as a base point image based on the first distance and the second distance.

13. The system of claim 9, wherein the processor is further configured to:
obtain a first vector from the geometric center to the first point image in the two-dimensional coordinate system;
obtain a second vector from the geometric center to the second point image in the two-dimensional coordinate system; and
associate the second point image with the second point based on a cross product of the first vector and the second vector and a dot product of the first vector and the second vector.

14. The system of claim 9, wherein the processor is further configured to issue a first command to move the robotic arm assembly to a safety point in response to identifying the movement of the patient and a second command to move the robotic arm assembly from the safety point to an operation target of the patient based on the updated operation pathway.

15. A non-transitory computer-readable storage medium containing a set of executable instructions which, in response to execution by a processor, cause the processor to perform a method to update an operation pathway for a robotic arm assembly to perform an operation on a patient having a predetermined spatial relationship with a frame including a tag in response to a movement of the patient, the method comprising:
processing a two-dimensional image associated with the tag having the spatial relationship with the patient, wherein a corresponding movement of the tag in response to the movement of the patient is determined based on the spatial relationship, and wherein the tag includes a first point and a second point, and the two-dimensional image includes a first point image and a second point image;
associating the first point image with the first point and the second point image with the second point; and
updating the operation pathway based on a conversion matrix of the first point and the second point, and the first point image and the second point image.

* * * * *